United States Patent
Wood et al.

(10) Patent No.: US 10,874,185 B2
(45) Date of Patent: *Dec. 29, 2020

(54) PROCESS FOR ONE-STEP COLOURING AND STRAIGHTENING HAIR

(71) Applicant: Kao Corporation, Tokyo (JP)

(72) Inventors: Jonathan Wood, Weinheim (DE); Burkhard Rose, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/780,186

(22) PCT Filed: May 9, 2014

(86) PCT No.: PCT/EP2014/059539
§ 371 (c)(1),
(2) Date: Sep. 25, 2015

(87) PCT Pub. No.: WO2014/180980
PCT Pub. Date: Nov. 13, 2014

(65) Prior Publication Data
US 2016/0051023 A1     Feb. 25, 2016

(30) Foreign Application Priority Data

May 10, 2013   (EP) ..................................... 13167317

(51) Int. Cl.
| | | |
|---|---|---|
| *A61Q 5/06* | (2006.01) | |
| *A45D 7/06* | (2006.01) | |
| *A61K 8/41* | (2006.01) | |
| *A61Q 5/04* | (2006.01) | |
| *A61K 8/365* | (2006.01) | |
| *A61K 8/36* | (2006.01) | |
| *A61K 8/46* | (2006.01) | |
| *A61K 8/49* | (2006.01) | |
| *A61Q 5/10* | (2006.01) | |
| *A45D 7/00* | (2006.01) | |

(52) U.S. Cl.
CPC ................ *A45D 7/06* (2013.01); *A61K 8/36* (2013.01); *A61K 8/365* (2013.01); *A61K 8/418* (2013.01); *A61K 8/466* (2013.01); *A61K 8/4946* (2013.01); *A61Q 5/04* (2013.01); *A61Q 5/065* (2013.01); *A61Q 5/10* (2013.01); *A45D 2007/001* (2013.01); *A45D 2007/008* (2013.01); *A61K 2800/4324* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 8,513,200 B2 * | 8/2013 | Dixon | A61K 8/042 514/20.7 |
| 9,844,500 B2 * | 12/2017 | Mannozzi | A45D 7/06 |
| 2002/0192175 A1 | 12/2002 | Patel et al. | |
| 2005/0102770 A1 | 5/2005 | Kiyomine et al. | |
| 2006/0222614 A1 * | 10/2006 | Buck | A61K 8/604 424/70.7 |
| 2009/0165812 A1 * | 7/2009 | Resnick | A61K 8/33 132/205 |
| 2010/0300471 A1 | 12/2010 | Malle et al. | |
| 2011/0052520 A1 * | 3/2011 | Nguyen | A61K 8/41 424/70.4 |
| 2013/0167861 A1 * | 7/2013 | Lopez | A61K 8/42 132/204 |
| 2013/0306095 A1 * | 11/2013 | Syed | A61K 8/447 132/204 |
| 2015/0305469 A1 * | 10/2015 | Paul | A61K 8/342 132/206 |
| 2016/0008251 A1 * | 1/2016 | Rose | A61K 8/36 132/206 |

FOREIGN PATENT DOCUMENTS

| | | | |
|---|---|---|---|
| EP | 2191 864 | * | 6/2010 |
| EP | 2 258 337 A1 | | 12/2010 |
| GB | 1 416 564 | | 12/1975 |
| JP | 2009-537620 A | | 10/2009 |
| WO | WO-00/38632 A1 | | 7/2000 |
| WO | WO-2011/104282 A2 | | 9/2011 |
| WO | WO-2012/010351 A2 | | 1/2012 |
| WO | WO-2013098211 A2 * | 7/2013 | ............. A61Q 5/065 |
| WO | WO-2014072645 A1 * | 5/2014 | ............. A61K 8/416 |

OTHER PUBLICATIONS

Reina Ikuyama, "Heat damage and the prevention technology of the hair," Fragrance Journal, pp. 45-50 (Nov. 2010).
"Surgical Operation Aid, Device," Latest Hair Color Technology, pp. 245-246 (Aug. 25, 2004).
"Glyoxylic acid", Wikipedia, May 8, 2013, XP055085717, Retrieved from the Internet: URL: http://en.wikipedia.org/wiki/Glyoxylicacid.
Extended European Search Report issued in Application No. 13167317.0 dated Nov. 6, 2013.
International Search Report and Written Opinion issued in International Application No. PCT/EP/2014/059539 dated Oct. 6, 2014.

* cited by examiner

*Primary Examiner* — Jyothsna A Venkat
(74) *Attorney, Agent, or Firm* — Foley & Lardner LLP

(57) ABSTRACT

The present invention provides a method which achieves a simultaneous coulouring and straightening of the hair in a single step, utilizing a hair treatment composition comprising at least one carboxylic acid of formula (I) defined below and at least one direct dye:

R—CO—COOH                               Formula (I)

In another aspect, the invention is directed to the hair treatment composition and the use thereof for straightening and colouring the hair.

3 Claims, No Drawings

PROCESS FOR ONE-STEP COLOURING AND STRAIGHTENING HAIR

FIELD OF THE INVENTION

The present invention relates to a method for colouring and semipermanent straightening of the hair.

BACKGROUND OF THE INVENTION

A known method for straightening curly or frizzy hair involves the use of straightening irons. The high temperature of the iron leads to a breakage of hydrogen bonds in the keratin of the hair, achieving a temporary straightening. The hydrogen bonds are formed again by the action of moisture, so that the hair reverts back to its original shape over the time because of air humidity, and the straightening effect vanishes after washing the hair.

The shape of the hair is largely determined by the disulfide bonds linking two cysteine moieties of the hair keratin. In order to achieve a more permanent shaping of the hair, known methods involve the cleavage of the disulfide bonds by the action of a sulfide- or thio group containing reducing agent. After the hair has been brought into the desired shape, new disulfide bonds are formed by applying an oxidizing agent such as hydrogen peroxide, thus fixing the shape of the hair. The use of such agents, however, may cause damage to the hair.

As an example for this kind of hair shaping treatment, reference is made to GB 1 416 564, describing reducing compositions comprising thioglycolates or thiolactates as reducing agents and fixing compositions comprising hydrogen peroxide as an oxidizing agent. The reducing compositions may further comprise a salt of an acid such as glyoxylic acid as a buffering agent.

As an alternative to the above-described two-step reduction and oxidation process, the disulfide bridges can be cleaved by the action of an alkaline agent such as sodium hydroxide at a pH of about 11 or higher. Under these conditions, the disulfide (or cystin) moiety can undergo a disproportionation reaction under the elimination of sulfur, and is cleaved into an alpha-beta-unsaturated dehydro-alanine moiety and a cysteine moiety. After the hair has been brought into the desired shape, the dehydro-alanin moieties and the cysteine moieties form thioether bonds and combine to lanthionine, stabilizing the straightened state of the hair. Since the disulfide or cystin moieties are converted into lanthionine moieties, this type of hair straightening process using an alkaline agent is also called lanthionization.

Both the two-stage reduction/oxidation method and the lanthionization method involve a cleavage of the disulfide bonds by a sulfur-based reducing agent or strong alkali, followed by the formation of new bonds among the hair proteins, leading to an irreversible change of the shape of the hair. This means that these processes can achieve a permanent straightening, wherein the treated portion of the hair maintains its shape, and the straightening effect only vanishes because of the growth of the hair.

Recently, it has been found that carboxylic acids having a carbonyl group adjacent to the carboxy group, such as glyoxylic acid, which are known as a buffering agent in cosmetic compositions, may have a semi-permanent straightening effect when used in combination with mechanical straightening means.

In this respect, WO 2011/104282 describes a process for semi-permanent hair straightening, which involves applying a composition comprising an α-keto acid onto the hair, leaving the composition in contact with the hair for 15 to 120 minutes, drying the hair and straightening the hair with a straightening iron at a temperature of 200±50° C.

Furthermore, WO 2012/010351 describes a treatment for semi-permanent straightening of curly, frizzy or wavy hair by applying a solution of glyoxylic acid in combination with mechanical straightening, using a straightening iron at a temperature of 200±30° C. After the treatment, the hair is said to retain its shape for at least six consecutive washings.

Hair dyeing methods and agents may be categorized in accordance with the type of the dye and the permanency of the color on hair. Depending on the permanency of the colour, hair dyes are usually classified as "permanent", "demi-permanent", "semi-permanent" or "temporary".

Permanent and demi-permanent dyeing is typically performed with oxidation dyes, which are formed from low molecular intermediates known as "precursors" and "couplers" by oxidative coupling thereof. The intermediates are small enough to penetrate into the hair, while after the application of the oxidizing agent, the larger dye molecule formed by the oxidative coupling stays trapped inside the hair.

Conversely, in case of direct dyes, the actual dye molecule is applied to the hair directly and adheres to the hair surface because of, for example, electrostatic interactions. In contrast to the oxidation dye intermediates, the penetration of the direct dyes into the hair is relatively poor because of the larger molecule size. As a result, direct dyes can be washed out, so that the colouring is merely temporary.

Some direct dyes, in particular nitro dyes, may adhere more firmly to the hair and may penetrate deeper into the hair surface to some extent. Colouring compositions comprising these dyes are washed out less easily and thus are termed "semi-permanent".

SUMMARY OF THE INVENTION

The present invention relates to a process for treating hair, characterized in that it comprises the following steps:
(a) application of a hair treatment composition (Dyeing/Straightening Composition) comprising at least one direct dye and at least one carboxylic acid of the formula (I) and/or a hydrate thereof and/or a salt thereof onto the hair:

R—CO—COOH                Formula (I)

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy,
(b) leaving the composition on the hair for 1 to 120 minutes;
(b') optionally rinsing off the hair;
(c) drying the hair; and
(d) treating the hair with an iron having a surface temperature of 180±50° C.
(e) optionally rinsing off and/or shampooing the hair and drying.

In another aspect, the present invention relates to the hair treatment composition as defined above, and the use thereof for the straightening and colouring of hair in a single treatment.

DETAILED DESCRIPTION OF THE INVENTION

The combination of such straightening and hair dyeing methods has not yet been described in the state of the art.

Conventionally, colouring and straightening treatment of the hair is carried out in two separate steps, which is time consuming and uneconomical for end users. Besides, there is also need for improving durability of the colours obtained with direct dye compositions.

The present invention solves these problems by providing a method which achieves a simultaneous coulouring and straightening of the hair in a single step.

For this purpose, the method of the present invention uses a hair treatment composition comprising at least one carboxylic acid of formula (I) defined below and at least one direct dye.

Surprisingly, it has been found that the carboxylic acid of formula (I) and the dye can be applied to the hair simultaneously without adverse interactions. On the contrary, the use of the hair treatment composition in accordance with the present invention unexpectedly yields an improvement of the colour durability on hair.

1. The Dyeing/Straightening Composition

The dyeing/straightening composition (in the following termed "treatment composition") comprises at least one carboxylic acid of the formula (I) and/or a hydrate thereof and/or a salt thereof, in combination with at least one direct dye. Preferable examples and amounts of the acid and the dye are explained in detail below.

Besides, the treatment composition may also comprise at least one surfactant and/or at least one conditioning component. Appropriate examples and amounts thereof are explained in detail below. For promoting the ease of use, it is preferable to include a silicone, preferably an amodimethicone, and/or a cationic polymer into the composition.

The treatment composition may suitably be in the form of a solution, emulsion, cream, gel, paste and mousse. Preferably, the composition is formulated as an aqueous solution.

The pH of the treatment composition is usually below or equal to 4.0, preferably in the range of 0.5 to 3, more preferably 1 to 2.5, as measured directly and at ambient temperature (25° C.). The pH of the composition may be adjusted using known alkaline solutions, preferably with sodium hydroxide solution.

In case it becomes necessary because of potential incompatibilities among the ingredients and/or in order to improve the stability of the composition during long term storage, the dyeing/straightening composition may also be prepared by mixing two separately stored parts, Parts A and B, prior to application onto the hair, wherein Part A comprises the carboxylic acid of the formula (I), while Part B comprises at least one direct dye.

Any surfactants and conditioning components as well as ingredients such as fragrances are preferably added to Part B.

2. The Carboxylic Acid of Formula (I)

The treatment composition comprises at least one carboxylic acid of the following formula (I) as the active component for achieving the straightening effect:

$$R-CO-COOH \quad \text{Formula (I)}$$

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy.

As preferred examples, glyoxylic acid, pyruvic acid and 2-ketobutyric acid can be mentioned.

The carboxylic acid of Formula (I) may be comprised in the composition in its free acid form. The carbonyl group adjacent to the acid group of the acid may also be present in the hydrate form. Apart from the free acid form and the hydrate thereof, salts of the acid or the hydrate may also be used.

The hydrate of the acid of Formula (I) may be formed when providing the composition as an aqueous solution. For instance, glyoxylic acid (H—CO—COOH) in aqueous solution is almost quantitatively present as the hydrate (H—C(OH)$_2$—COOH). Besides, the hydrate may also condense to dimers.

A salt of the carboxylic acid of Formula (I) may also be used. As examples, alkali metal salts such as the sodium or potassium salt, alkaline earth metal salts such as the magnesium salt or the calcium salt and ammonium salts may be mentioned.

In the present invention, glyoxylic acid is a preferred carboxylic acid of Formula (I).

The concentration of the at least one carboxylic acid of the formula (I) and/or a hydrate thereof and/or salts thereof is in the range of 0.1 to 40%, preferably 0.5 to 30%, more preferably 1 to 25% and even more preferably 2.5 to 20% by weight, based on the total weight of the treatment composition.

Conventional hair shaping/straightening techniques are based on the re-organization of the disulfide bridges and involve a cleavage of the disulfide bonds by using a sulfur-based reducing agent, followed by the shaping of the hair and the formation of new disulfide bonds by the action of an oxidizing agent. In contrast, the present invention does not utilize cleavage of the disulfide bonds and fixing the bonds in the new shape. Therefore, the treatment composition of the present invention does not require the presence of sulfur-based reducing agents. However, up to 2% by weight calculated to the total of the composition sulfur based reducing agents does not disturb the straightening performance of the compositions. Therefore, the treatment composition has less than 2% by weight of sulfur-based reducing agents, and preferably is free of sulfur-based reducing agents.

3. The Direct Dye

In the present invention, there are no particular limitations as to the type of direct dye, and any direct dye suitable for hair colouring may be used. Examples of the direct dye include an anionic dye, a nitro dye, a disperse dye, and a cationic dye and mixtures thereof.

Non-limiting examples of the cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87 and mixtures thereof. Particularly preferred are Basic Red 51, Basic Orange 31, Basic Yellow 87 and mixtures thereof.

Non-limiting examples of the anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as the sodium or potassium salt and mixtures thereof.

Among those, the preferred anionic dyes are Acid Red 52, Acid Violet 2, Acid Red 33, Acid Orange 4, Acid Red 27 and Acid Yellow 10 and their salts. Even more preferred anionic dyes are Acid Red 52, Acid Violet 2, Acid Red 33, Acid Orange 4 and Acid Yellow 10, and their salts and mixtures thereof.

Non-limiting examples for the nitro dye are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid and mixtures thereof.

The treatment composition may suitably comprise only one direct dye or a combination of direct dyes. In this respect, direct dyes of different ionic characters may also be comprised in the same composition.

The total amount of direct dye in the treatment composition is within the range of 0.001 to 10%, preferably 0.01 to 7.5%, more preferably 0.05 to 5% by weight, based on the total weight of the treatment composition.

4. Surfactant

The treatment composition may comprise a surfactant. As the surfactant, any of a cationic surfactant, a nonionic surfactant, an amphoteric surfactant and an anionic surfactant can be used. It is also possible to use two or more types of surfactants in combination.

The cationic surfactant is preferably a mono-long chain alkyl quaternary ammonium salt, having a $C_8$-$C_{24}$ alkyl residue and three $C_1$-$C_4$ alkyl residues.

Preferably at least one mono alkyl quaternary ammonium surfactant is selected from the compounds with the general formula

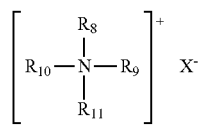

wherein $R_8$ is a saturated or unsaturated, branched or straight alkyl chain with 8-22 C atoms or

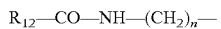

wherein $R_{12}$ is a saturated or unsaturated, branched or straight alkyl chain with 7-21 C atoms and n is an integer of 1-4, or

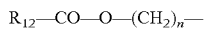

wherein $R_{12}$ is a saturated or unsaturated, branched or straight alkyl chain with 7-21 C atoms and n is an integer of 1-4, and $R_9$, $R_{10}$ and $R_{11}$ are independent from each other an alkyl group with 1 to 4 carbon atoms, hydroxyl alky chain with 1 to 4 carbon atoms, or ethoxy or propoxy group with a number of ethoxy or propoxy groups varying in the range of 1 to 4, and X is chloride, bromide, methosulfate or ethosulfate.

Suitable cationic surfactants are, for example, long-chain quaternary ammonium compounds which can be used alone or in admixture with one another, such as cetyl trimethyl ammonium chloride, myristyl trimethyl ammonium chloride, behentrimonium chloride, trimethyl cetyl ammonium bromide, stearyl trimethyl ammonium chloride, stearyl trimonium chloride and stearamidopropyltrimonium chloride.

Examples of the nonionic surfactant include polyoxy-$C_{1-4}$-alkylene $C_{8-24}$-alkyl ether, polyoxy-$C_{1-4}$-alkylene $C_{8-24}$-alkylene alkenyl ether, higher ($C_{12}$-$C_{24}$) fatty acid sucrose ester, polyglycerin $C_{8-24}$-fatty acid ester, higher ($C_{12}$-$C_{24}$) fatty acid mono- or diethanolamide, polyoxyethylene hardened castor oil, polyoxyethylene sorbitan $C_{8-24}$-fatty acid ester, polyoxyethylene sorbit $C_{8-24}$-fatty acid ester, $C_{8-24}$-alkyl saccharide surfactant, $C_{8-24}$-alkylamine oxide, and $C_{8-24}$-alkylamidoamine oxide.

Examples of the amphoteric surfactant include an imidazoline-based surfactant, a carbobetaine-based surfactant, an amidobetaine-based surfactant, a sulfobetaine-based surfactant, a hydroxysulfobetaine-based surfactant and an amidosulfobetaine-based surfactant.

Examples of the anionic surfactant include alkylbenzenesulfonate, alkyl or alkenyl ether sulfate, alkyl or alkenyl sulfate, olefin sulfonate, alkanesulfonate, saturated or unsaturated fatty acid salts, alkyl or alkenyl ether carboxylate, α-sulfo fatty acid salts, N-acylamino acid type surfactants, phosphoric acid mono- or diester type surfactants, and sulfosuccinate. Examples of the alkyl ether sulfate include polyoxyethylene alkyl ether sulfate. Examples of the counterion for the anionic residues of these surfactants include an alkalimetal ion such as sodium ion or potassium ion; an alkaline earth metal ion such as calcium ion or magnesium ion; an ammonium ion; and an alkanolamine having 1 to 3 alkanol groups each having 2 or 3 carbon atoms (for example, monoethanolamine, diethanolamine, triethanolamine, or triisopropanolamine).

The surfactant can be used singly or in combination of two or more kinds. When adding a surfactant to the treatment composition, the content thereof usually is 0.05 to 10% wt. %, more preferably 0.1 to 5 wt. %, based on the total weight of the treatment composition.

5. Conditioning Component

The treatment composition may optionally comprise a conditioning component suitable for application to the hair. The conditioning component is an oil or polymer which adheres to the hair and improves the feel and the manageability.

When using the conditioning component, the total amount thereof is preferably 0.01 to 30 wt. %, more preferably 0.05 to 20 wt. %, and even more preferably 0.1% to 10 wt. %, based on the total weight of the treatment composition.

Examples of the conditioning component generally include cationic polymers, silicones, higher alcohols, and organic conditioning oils (for example, hydrocarbon oil, polyolefin and fatty acid ester). The composition may comprise a single type of conditioning component, or two or more in combination.

Cationic Polymers

A cationic polymer is a polymer having a cationic group or a group capable of being ionized into a cationic group, and in general, an amphoteric polymer acquiring net cationic charge is also included in the terminology. That is, the cationic polymer is a polymer containing an amino group or an ammonium group in a side chain of the polymer chain, or a polymer including a diallyl quaternary ammonium salt as a constituent unit, and examples thereof include cationized cellulose, cationic starch, cationic guar gum, a polymer or copolymer of a diallyl quaternary ammonium salt, and quaternized polyvinylpyrrolidone. Among these, from the viewpoint of softness, smoothness and easy finger-combing during shampooing, and easy manageability and moisture retention during drying, and from the viewpoint of stability of the agent, a polymer including a diallyl quaternary ammonium salt as a constituent unit, quaternized polyvinylpyrrolidone, and cationized cellulose are preferred, and a polymer or copolymer of a diallyl quaternary ammonium salt, and cationized cellulose are more preferred.

Specific examples of the polymer or copolymer of a diallyl quaternary ammonium salt include dimethyldiallylammonium chloride polymer (polyquaternium-6, for example, MERQUAT 100; Nalco Company), dimethyldiallylammonium chloride/acrylic acid copolymer (polyquaternium-22, for example, MERQUAT 280, MERQUAT 295; Nalco Company), and dimethyldiallylammonium chloride/acrylic acid amide copolymer (polyquaternium-7, for example, MERQUAT 550; Nalco Company).

Specific examples of the quaternized polyvinylpyrrolidone include quaternary ammonium salts synthesized from a copolymer of vinylpyrrolidone (VP) and dimethylaminoethyl methacrylate, and diethyl sulfate (polyquaternium 11, for example, GAFQUAT 734, GAFQUAT 755 and GAFQUAT 755N (all by ISP Japan, Ltd.)).

Specific examples of the cationized cellulose include a polymer of a quaternary ammonium salt obtained by adding glycidyltrimethylammonium chloride to hydroxyethylcellulose (polyquaternium-10, for example, RHEOGUARD G and RHEOGUARD GP (all by Lion Corp.), POLYMER JR-125, POLYMER JR-400, POLYMER JR-30M, POLYMER LR-400 and POLYMER LR-30M (all by Amerchol Corp.)), and a hydroxyethylcellulose/dimethyldiallylammonium chloride copolymer (polyquaternium-4, for example, CELQUAT H-100, CELQUAT L-200 (all by National Starch and Chemical Company)).

The cationic polymer may be used in combination of two or more kinds. Furthermore, the cationic polymer gives better effects when the content is increased, but an excessively high content of the cationic polymer may cause stability failure and a decrease in the viscosity of the agent alone or during mixing. From this viewpoint, and from the viewpoint of enhancing the feel to the touch, the content of the cationic polymer is preferably 0.001 to 20 wt %, more preferably 0.01 to 10 wt. %, and even more preferably 0.05 to 5 wt. %, based on the total weight of the treatment composition.

Silicones

In order to improve the feel of use, the treatment composition preferably contains a silicone. Examples of the silicone include dimethylpolysiloxane, and modified silicone (for example, amino-modified silicone, fluorine-modified silicone, alcohol-modified silicone, polyether-modified silicone, epoxy-modified silicone, or alkyl-modified silicone), but dimethylpolysiloxane, polyether-modified silicone and amino-modified silicone are preferred.

The dimethylpolysiloxane may be any cyclic or non-cyclic dimethylsiloxane polymer, and examples thereof include SH200 series, BY22-019, BY22-020, BY11-026, B22-029, BY22-034, BY22-050A, BY22-055, BY22-060, BY22-083, FZ-4188 (all by Dow Corning Toray Co., Ltd.), KF-9008, KM-900 series, MK-15H, and MK-88 (all by Shin-Etsu Chemical Co., Ltd.).

The polyether-modified silicone may be any silicone having a polyoxyalkylene group, and the group constituting the polyoxyalkylene group may be an oxyethylene group or an oxypropylene group. More specific examples include KF-6015, KF-945A, KF-6005, KF-6009, KF-6013, KF-6019, KF-6029, KF-6017, KF-6043, KF-353A, KF-354A, KF-355A (all by Shin-Etsu Chemical Co., Ltd.), FZ-2404, SS-2805, FZ-2411, FZ-2412, SH3771M, SH3772M, SH3773M, SH3775M, SH3749, SS-280X series, BY22-008 M, BY11-030, and BY25-337 (all by Dow Corning Toray Co., Ltd.).

The amino-modified silicone may be any silicone having an amino group or an ammonium group, and examples thereof include an amino-modified silicone oil having all or a part of the terminal hydroxyl groups capped with a methyl group or the like, and an amodimethicone which does not have the terminals capped. A preferred example of the amino-modified silicone may be a compound represented by the following formula:

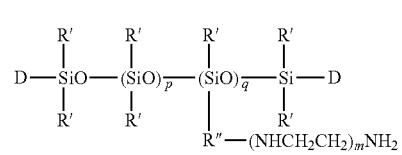

(S)

wherein R' represents a hydroxyl group, a hydrogen atom or $R^x$; $R^x$ represents a substituted or unsubstituted monovalent hydrocarbon group having 1 to 20 carbon atoms; D represents $R^x$, $R''$—$(NHCH_2CH_2)_mNH_2$, $OR^x$, or a hydroxyl group; R" represents a divalent hydrocarbon group having 1 to 8 carbon atoms; m represents a number from 0 to 3; p and q represent numbers, the sum of which is, as a number average, equal to or greater than 10 and less than 20,000, preferably equal to or greater than 20 and less than 3000, more preferably equal to or greater than 30 and less than 1000, and even more preferably equal to or greater than 40 and less than 800.

Specific examples of suitable commercially available products of the amino-modified silicone include amino-modified silicone oils such as SF8452C, SS-3551 (all by Dow Corning Toray Co., Ltd.), KF-8004, KF-8675, and KF-8015 (all by Shin-Etsu Chemical Co., Ltd.); and amodimethicone emulsions such as SM8704C, SM8904, BY22-079, FZ-4671, and FZ-4672 (all by Dow corning Toray Co., Ltd.).

The total content of these silicones in the treatment composition of the present invention is usually 0.1 to 20 wt.

%, preferably 0.2% to 10 wt. % and more preferably 0.5 to 5 wt. %, based on the total weight of the treatment composition.

Oil Component

For improving the feel upon use, the treatment composition may also include an organic conditioning oil. The organic conditioning oil that is suitably used as a conditioning component is preferably a low-viscosity and water-insoluble liquid, and is selected from a hydrocarbon oil having at least 10 carbon atoms, a polyolefin, a fatty acid ester, a fatty acid amide, a polyalkylene glycol, and mixtures thereof. The viscosity of such an organic conditioning oil as measured at 40° C. is preferably 1 to 200 mPa·s, more preferably 1 to 100 mPa·s, and even more preferably 2 to 50 mPa·s. For the determination of the viscosity, a capillary viscometer may be used.

Examples of the hydrocarbon oil include a cyclic hydrocarbon, a linear aliphatic hydrocarbon (saturated or unsaturated), and a branched aliphatic hydrocarbon (saturated or unsaturated), and polymers or mixtures thereof are also included. The linear hydrocarbon oil preferably has 12 to 19 carbon atoms. The branched hydrocarbon oil includes hydrocarbon polymers, and preferably has more than 19 carbon atoms.

The polyolefin is a liquid polyolefin, more preferably a liquid poly-α-olefin, and even more preferably a hydrogenated liquid poly-α-olefin. The polyolefin used herein is prepared by polymerizing an olefin monomer having 4 to 14 carbon atoms, and preferably 6 to 12 carbon atoms.

The fatty acid ester may be, for example, a fatty acid ester having at least 10 carbon atoms. Examples of such a fatty acid ester include esters having a hydrocarbon chain derived from a fatty acid and an alcohol (for example, monoesters, polyhydric alcohol esters, or di- and tricarboxylic acid esters). The hydrocarbon group of these fatty acid esters may have another compatible functional group such as an amide group or an alkoxy group as a substituent, or the hydrocarbon group may be covalently bonded to those functional groups. More specifically, an alkyl and alkenyl ester of a fatty acid having a fatty acid chain having 10 to 22 carbon atoms, a carboxylic acid ester of an aliphatic alcohol having an aliphatic chain derived from an alkyl and/or alkenyl alcohol having 10 to 22 carbon atoms, and a mixture thereof are suitably used. Specific examples of these preferred fatty acid esters include isopropyl isostearate, hexyl laurate, isohexyl laurate, isohexyl palmitate, isopropyl palmitate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate and dioleyl adipate.

Further suitable oil components are natural oils such as paraffin oil and natural triglycerides.

Suitable natural triglycerides are argan oil, Shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil.

The organic conditioning oil may be used in combination of two or more kinds, and the total concentration is typically in the range of 0.1 to 20 wt. %, preferably 0.2 to 10 wt. %, more preferably 0.5 to 5 wt. %, based on the total weight of the treatment composition.

Fatty Alcohols

From the viewpoint of improving the sense of touch and stability, the treatment composition may also contain a higher alcohol having 8 carbon atoms or more. Usually, the higher alcohol has 8 to 22 carbon atoms, and preferably 16 to 22 carbon atoms. Specific examples thereof include cetyl alcohol, stearyl alcohol, behenyl alcohol, and mixtures thereof.

The higher alcohol may be used in combination of two or more kinds, and the content thereof is typically 0.1 to 20 wt. %, preferably 0.2 to 10 wt. %, more preferably 0.5 to 5 wt. %, based on the total weight of the treatment composition.

Additionally polyols may suitably be comprised in the compositions. Examples of the polyalkylene glycol include polyethylene glycol and polypropylene glycol, and a mixture of the two may be used, or a copolymer of ethylene oxide and propylene oxide may also be used.

6. Hair Treatment Process

In step (a), the treatment composition is applied to the hair. The application weight ratio of hair to composition is 0.5:2 to 2:0.5, preferably 0.5:1 to 1:0.5, more preferably about 1:1.

If the composition is provided in a two-part form, the respective parts A and B are preferably mixed directly before application to the hair.

Subsequent to the application, the treatment composition is left on the hair for 1 to 120 minutes, preferably 5 to 90 minutes, more preferably 10 to 60 minutes and even more preferably 15 to 45 minutes at a temperature of 45° C. or below, preferably at ambient temperature (step (b)). Then, the straightening composition is optionally rinsed off from the hair (step (b')).

In subsequent step (c), the hair is dried in order to avoid an excessive steam generation in the subsequent step of treating the hair with the iron. Typically, a hair dryer is used for this purpose. It is preferable to dry the hair under continuous combing in order to prevent entanglement of the hair.

Subsequent to the drying, the hair is treated with an iron having a surface temperature of 180±50° C., preferably 170 to 200° C. A usual straightening iron may be used for this purpose (step (d)).

The following examples further describe and demonstrate embodiments of the present invention. The examples are given solely for the purpose of illustration and are not to be construed as limitations of the present invention.

EXAMPLES

Example 1

An aqueous hair treatment composition comprising anionic dyes is formulated by mixing the following ingredients:
10.00 wt. %—Glyoxylic Acid
1.50 wt. %—Amodimethicone
1.40 wt. %—Hydroxyethylcellulose
0.30 wt. %—Fragrance
0.55 wt. %—Acid Red 52/C.I. 45100
0.28 wt. %—Orange 4/Acid Orange 7/C.I. 15510
0.01 wt. %—Ext. Violet 2/Acid Violet 43/C.I. to 100 wt. %—Water Example 2

An aqueous hair treatment composition comprising cationic dyes is formulated by mixing the following ingredients:
10.00 wt. %—Glyoxylic Acid
1.50 wt. %—Amodimethicone 1.40 wt. %—Hydroxyethylcellulose
0.30 wt. %—Fragrance
0.55 wt. %—Basic red 51
0.28 wt. %—Basic yellow 87
0.01 wt. %—Basic orange 31 to 100 wt. %—Water Example 3

An aqueous hair treatment composition comprising nitro dyes is formulated by mixing the following ingredients:
10.00 wt. %—Glyoxylic Acid
1.50 wt. %—Amodimethicone
1.40 wt. %—HYdroxyethylcellulose
0.30 wt. %—Fragrance/Parfum
0.55 wt. %—HC Red 3
0.28 wt. %—HC Yellow 2 to 100 wt. %—Water Example 4

An aqueous hair treatment composition comprising a combination of an anionic dye, a cationic dye and a nitro dye is prepared by mixing the following ingredients:
10.00 wt. %—Glyoxylic Acid
1.50 wt. %—Amodimethicone
1.40 wt. %—Hydroxyethylcellulose
0.30 wt. %—Fragrance/Parfum
0.55 wt. %—Basic red 51
0.28 wt. %—Acid red 52
0.010 wt. %—HC red 3 to 100 wt. %—Water Example 5

Nitro Dye

A dyeing/straightening composition according to the present invention of 0.10% HC Red BN in an aqueous solution of 5.0% glyoxylic acid and a comparative composition comprising of 0.10% HC Red BN in an aqueous solution of 5.0% lactic acid were prepared. In both compositions, the pH has been adjusted to 2.0 with sodium hydroxide.

Streaks of white goat hair (1 g each) were treated either with the composition according to the present invention or with the reference composition. The compositions were applied to the streaks using a pipet (5 ml/streak), distributed uniformly and left on the sample for 20 minutes at 40° C. Then, the samples were rinsed off with water and dried in the air for 60 minutes. Afterwards, the initial colour values in the L*a*b-system were determined. The ironing was subsequently performed using a flat iron heated to a temperature of 180° C.

After the ironing, the wash-fastness of the colour was evaluated. Each streak was placed into a glass bottle with 100 ml of a cleansing solution containing 3 wt. % of Na-SLES as a surfactant and subjected to shaking for 20 minutes at 30° C. and a shaking rate of 100 min$^{-1}$. Then, the wash-fastness was evaluated by visually inspecting the samples, measuring the colour values in the L*a*b-system and calculating the difference with respect to the initial values.

Visual inspection showed that the colour was somewhat lighter in case of the inventive composition and remarkably lighter in case of the comparative composition. Quantitatively, the inventive composition yielded a difference of the colour values of $\Delta L=5.87$ and $\Delta a=4.61$, while the comparative composition yielded $\Delta L=8.64$ and $\Delta a=8.29$.

Example 6

Cationic Dye

A dye/straightening composition according to the present invention of 1.00% Basic Red 51 in an aqueous solution of 5.0% glyoxylic acid and a comparative composition comprising of 1.00% Basic Red 51 in an aqueous solution of 5.0% lactic acid were prepared. In both compositions, the pH has been adjusted to 2.0 with sodium hydroxide.

Streaks of bleached yak hair (1 g each) were treated either with the composition according to the present invention or with the reference composition. The compositions were applied to the streaks using a pipet (5 ml/streak) and distributed uniformly with a brush.

Then, the samples were covered with a plastic foil, and incubated in an oven for 20 minutes at 40° C. Afterwards, the samples were rinsed off with water and dried in the air for 60 minutes at ambient temperature, and the initial color values in the L*a*b-system were determined. The ironing was subsequently performed using a flat iron (BaByliss™ PRO Must Styler Type C100a) heated to a temperature of 180° C. (5 strokes, time: 7s).

After the ironing, the wash-fastness of the colour was evaluated. Each streak was placed into a glass bottle with 100 ml of a cleansing solution containing 3 wt. % of Na-LES as a surfactant and subjected to shaking for 40 minutes at 30° C. and a shaking rate of 100 min$^{-1}$. Then, the wash-fastness was evaluated by visually inspecting the samples, measuring the color values in the L*a*b-system and calculating the difference with respect to the initial values.

Visual inspection showed that the colour was somewhat lighter in case of the inventive composition and remarkably lighter in case of the comparative composition. Quantitatively, the inventive composition yielded a difference of the colour intensity of $\Delta L=8.63$ and overall colour difference of $\Delta E=15.61$, while the comparative composition yielded $\Delta L=22.09$ and $\Delta E=30.78$.

Example 7

Anionic Dye

A dye/straightening composition according to the present invention of 0.10% Acid Yellow 1 in an aqueous solution of 5.0% glyoxylic acid and a comparative composition comprising of 0.10% Acid Yellow 1 in an aqueous solution of 5.0% lactic acid were prepared. In both compositions, the pH has been adjusted to 2.0 with sodium hydroxide.

Streaks of bleached yak hair (1 g each) were treated either with the composition according to the present invention or with the reference composition. The compositions were applied to the streaks using a pipet (5 ml/streak) and distributed uniformly with a brush.

Then, the samples were covered with a plastic foil, and incubated in an oven for 20 minutes at 40° C. Afterwards, the samples were rinsed off with water and dried in the air for 60 minutes at ambient temperature, and the initial color values in the L*a*b-system were determined. The ironing was subsequently performed using a flat iron (BaByliss™ PRO Must Styler Type C100a) heated to a temperature of 180° C. (5 strokes, time: 7s).

After the ironing, the wash-fastness of the colour was evaluated. Each streak was placed into a glass bottle with 100 ml of a cleansing solution containing 3 wt. % of Na-LES as a surfactant and subjected to shaking for 40 minutes at 30° C. and a shaking rate of 100 min$^{-1}$. Then, the wash-fastness was evaluated by visually inspecting the samples, measuring the color values in the L*a*b-system and calculating the difference with respect to the initial values.

Quantitatively, the inventive composition yielded a difference of the colour intensity value of ΔL=0.76 and overall colour difference of ΔE=3.54, while the comparative composition yielded values of ΔL=2.18 and ΔE=5.13.

The results of the tests in the Examples 5, 6 and 7 clearly show that a dyeing/straightening composition according to the present invention, comprising a direct dye in combination with a carboxylic acid of formula (I) such as glyoxylic acid, achieves a remarkable improvement of colour durability on hair.

The invention claimed is:

1. A process for simultaneously straightening and coloring hair, comprising the following steps:
    (a) application of a single hair treatment composition for straightening and coloring hair comprising a direct dye selected from the group consisting of an anionic direct dye, a cationic direct dye, and a nitro direct dye wherein the total amount of the direct dye is 0.01 to 7.5% by weight and glyoxylic acid at a total concentration in the range of 2.5 to 20% by weight based on the weight of the total single hair treatment composition onto the hair:
    (b) leaving the single hair treatment composition on the hair for 10 to 60 minutes;
    (b') optionally rinsing off the hair;
    (c) drying the hair; and
    (d) treating the hair with an iron having a surface temperature of 180 ±50° C.;
    (e) optionally rinsing off and/or shampooing the hair and drying,
    wherein the hair treatment composition has a pH of 1 to 3, wherein the single hair treatment composition is free of any sulfur-based reducing agents.

2. The process according to claim 1, wherein the single hair treatment composition further comprises a conditioning component selected from the group consisting of a silicone oil and a cationic polymer.

3. The process according to claim 1, wherein the temperature of the iron is in the range of 170 to 200° C.

* * * * *